United States Patent
Gambogi et al.

[11] Patent Number: 5,853,743
[45] Date of Patent: Dec. 29, 1998

[54] LIGHT DUTY LIQUID CLEANING COMPOSITIONS

[75] Inventors: Joan E. Gambogi, Belle Mead; Gary J. Jakubicki, Robbinsville; Leonard A. Zyzyck, Skillman, all of N.J.

[73] Assignee: Colgate Palmolive Company, Piscataway, N.J.

[21] Appl. No.: 906,684

[22] Filed: Aug. 5, 1997

[51] Int. Cl.$^6$ .................................... A01N 23/32
[52] U.S. Cl. ....................... 424/405; 510/426; 514/556
[58] Field of Search .................... 424/405, 406, 424/722, 60, 62, 76.1; 510/76.21, 235, 237, 245, 248, 260, 264, 280, 405, 499, 411, 414, 426; 514/556, 644

[56] References Cited

U.S. PATENT DOCUMENTS

| | | | |
|---|---|---|---|
| 3,720,629 | 3/1973 | Sharman | 252/161 |
| 3,882,038 | 5/1975 | Clayton et al. | 252/89 |
| 4,749,516 | 6/1988 | Brusky | 252/546 |
| 4,923,635 | 5/1990 | Simion et al. | 252/545 |
| 5,102,573 | 4/1992 | Han et al. | 252/153 |
| 5,171,475 | 12/1992 | Freisseleben | 252/312 |
| 5,252,245 | 10/1993 | Garabedian et al. | 252/152 |
| 5,302,377 | 4/1994 | Pereira et al. | 424/59 |
| 5,385,696 | 1/1995 | Repinec et al. | 252/550 |
| 5,387,375 | 2/1995 | Erilli et al. | 252/546 |
| 5,389,304 | 2/1995 | Repinec et al. | 252/546 |
| 5,389,305 | 2/1995 | Repinec et al. | 252/549 |
| 5,389,676 | 2/1995 | Michaels | 514/556 |
| 5,696,073 | 12/1997 | Jakubicki et al. | 510/426 |
| 5,700,773 | 12/1997 | Jakubicki et al. | 510/426 |
| 5,712,241 | 1/1998 | Gorlin et al. | 510/426 |

*Primary Examiner*—Thurman K. Page
*Assistant Examiner*—Kathryne E. Shelborne
*Attorney, Agent, or Firm*—Richard E. Nanfeldt; James M. Serafino

[57] ABSTRACT

A light duty liquid detergent with desirable cleansing properties and mildness to the human skin comprising: at least one sulfonate surfactant, an alkali metal or ammonium salt of a $C_{8-18}$ ethoxylated alkyl ether sulfate anionic surfactant, a betaine surfactant, an alkyl polyglucoside surfactant, an ethoxylated alkyl $C_{12}$–$C_{14}$ monoalkanol amide, optionally, $C_{12}$–$C_{14}$ monoalkanol amide and water.

6 Claims, No Drawings

LIGHT DUTY LIQUID CLEANING COMPOSITIONS

FIELD OF THE INVENTION

This invention relates to a light duty liquid cleaning composition which imparts enhanced mildness to the skin and is designed in particular for dishware and which is effective in removing grease soil and in leaving rinsed surfaces with a shiny appearance.

BACKGROUND OF THE INVENTION

The present invention relates to novel light duty liquid detergent compositions with high foaming properties, containing at least one sulfonate surfactant, an ammonium or alkali metal salt of an ethoxylated alkyl ether sulfate surfactant, an alkyl polyglucoside surfactant, a betaine surfactant, an ethoxylated alkyl monoalkanol amide, and amine oxide surfactant, a solubilizing system and water.

The prior art is replete with light duty liquid detergent compositions containing nonionic surfactants in combination with anionic and/or betaine surfactants wherein the nonionic detergent is not the major active surfactant, as shown in U.S. Pat. No. 3,658,985 wherein an anionic based shampoo contains a minor amount of a fatty acid alkanolamide. U.S. Pat. No. 3,769,398 discloses a betaine-based shampoo containing minor amounts of nonionic surfactants. This patent states that the low foaming properties of nonionic detergents renders its use in shampoo compositions non-preferred. U.S. Pat. No. 4,329,335 also discloses a shampoo containing a betaine surfactant as the major ingredient and minor amounts of a nonionic surfactant and of a fatty acid mono- or di-ethanolamide. U.S. Pat. No. 4,259,204 discloses a shampoo comprising 0.8–20% by weight of an anionic phosphoric acid ester and one additional surfactant which may be either anionic, amphoteric, or nonionic. U.S. Pat. No. 4,329,334 discloses an anionic-amphoteric based shampoo containing a major amount of anionic surfactant and lesser amounts of a betaine and nonionic surfactants.

U.S. Pat. No. 3,935,129 discloses a liquid cleaning composition based on the alkali metal silicate content and containing five basic ingredients, namely, urea, glycerin, triethanolamine, an anionic detergent and a nonionic detergent. The silicate content determines the amount of anionic and/or nonionic detergent in the liquid cleaning composition. However, the foaming property of these detergent compositions is not discussed therein.

U.S. Pat. No. 4,129,515 discloses a heavy duty liquid detergent for laundering fabrics comprising a mixture of substantially equal amounts of anionic and nonionic surfactants, alkanolamines and magnesium salts, and, optionally, zwitterionic surfactants as suds modifiers.

U.S. Pat. No. 4,224,195 discloses an aqueous detergent composition for laundering socks or stockings comprising a specific group of nonionic detergents, namely, an ethylene oxide of a secondary alcohol, a specific group of anionic detergents, namely, a sulfuric ester salt of an ethylene oxide adduct of a secondary alcohol, and an amphoteric surfactant which may be a betaine, wherein either the anionic or nonionic surfactant may be the major ingredient.

The prior art also discloses detergent compositions containing all nonionic surfactants as shown in U.S. Pat. Nos. 4,154,706 and 4,329,336 wherein the shampoo compositions contain a plurality of particular nonionic surfactants in order to effect desirable foaming and detersive properties despite the fact that nonionic surfactants are usually deficient in such properties.

U.S. Pat. No. 4,013,787 discloses a piperazine based polymer in conditioning and shampoo compositions which may contain all nonionic surfactant or all anionic surfactant.

U.S. Pat. No. 4,671,895 teaches a liquid detergent composition containing an alcohol sulfate surfactant, a nonionic surfactant, a paraffin sulfonate surfactant, an alkyl ether sulfate surfactant and water.

U.S. Pat. No. 4,450,091 discloses high viscosity shampoo compositions containing a blend of an amphoteric betaine surfactant, a polyoxybutylene polyoxyethylene nonionic detergent, an anionic surfactant, a fatty acid alkanolamide and a polyoxyalkylene glycol fatty ester. But, none of the exemplified compositions contains an active ingredient mixture wherein the nonionic detergent is present in major proportion, probably due to the low foaming properties of the polyoxybutylene polyoxyethylene nonionic detergent.

U.S. Pat. No. 4,595,526 describes a composition comprising a nonionic surfactant, a betaine surfactant, an anionic surfactant and a $C_{12}$–$C_{14}$ fatty acid monoethanolamide foam stabilizer.

U.S. Pat. Nos. 4,675,422; 4,698,181; 4,724,174; 4,770,815 and 4,921,942 disclose alkyl succinamates but the compositions are non related to light duty liquid compositions.

However, none of the above-cited patents discloses a liquid detergent composition containing at least one sulfonate surfactant, an alkali metal or ammonium salt of an ethoxylated alkyl ether sulfate surfactant, an alkyl polyglucoside surfactant, a betaine surfactant, an ethoxylated alkyl monoalkanol amide, an amine oxide, and water, wherein the composition does not contain any low molecular weight mono- or di-glucoside, abrasives, silicas, alkaline earth metal carbonates, alkyl glycine surfactant, ethoxylated nonionic surfactant, cyclic imidinium surfactant, alkali metal carbonates or more than 3 wt. % of a fatty acid or its salt thereof or an ethoxylated and/or propoxylated nonionic surfactant formed from a fatty alcohol and ethylene oxide and/or propylene oxide or a glycol ether cosurfactant or more than 0.25 of a water insoluble hydrocarbon such as a perfume or a grease release agent such as choline chloride.

SUMMARY OF THE INVENTION

It has now been found that a light duty liquid composition can be made which has desirable cleaning properties together with enhanced mildness to the human skin.

An object of this invention is to provide a novel light duty liquid detergent composition containing two sulfonate surfactants, an alkali metal salt or ammonium salt of an ethoxylated alkyl ether sulfate surfactant, an alkyl polyglucoside surfactant, a betaine surfactant, an ethoxylated alkyl monoalkanol amide, optionally, an alkyl monoalkanol amide, and water wherein the composition does not contain any silicas, abrasives, ethoxylated nonionic surfactant, alkali metal carbonates, alkaline earth metal carbonates, alkyl glycine surfactant, cyclic imidinium surfactant, low molecular weight mono- or di-glucoside organoaluminum containing compounds, organo titanium containing compounds, triethylene tetramine hexaacetic acid, imidazolenes, or more than 3 wt. % of a fatty acid or salt thereof or an ethoxylated and/or propoxylated nonionic surfactant formed from a fatty alcohol and ethylene oxide and/or propylene oxide or a glycol ether cosurfactant or more than 0.25 of a water insoluble hydrocarbon such as a perfume or a grease release agent such as choline chloride.

Another object of this invention is to provide a novel light duty liquid detergent with desirable high foaming and cleaning properties which is very mild to the human skin.

Additional objects, advantages and novel features of the invention will be set forth in part ire the description which follows, and in part will become apparent to those skilled in the art upon examination of the following or may be learned by practice of the invention. The objects and advantages of the invention may be realized and attained by means of the instrumentalities and combinations particularly pointed out in the appended claims.

DETAILED DESCRIPTION OF THE INVENTION

The light duty liquid compositions of the instant invention comprise approximately by weight:

(a) 4% to 18% of an alkali metal salt or ammonium salt of a $C_{8-18}$ ethoxylated alkyl ether sulfate;

(b) 1% to 14% of a first sulfonate surfactant which is a magnesium salt of a linear alkyl benzene sulfonate surfactant;

(c) 4% to 12% of a betaine surfactant;

(d) 0 to 8% of an amine oxide;

(e) 0.2% to 4% of an ethoxylated alkyl monoalkanol amide;

(f) 4% to 16% of an alkyl polyglucoside surfactant;

(g) 1% to 6% of a second sulfonate surfactant which is an alkali metal salt of a linear alkyl benzene sulfonate; and (h) the balance being water.

The $C_{8-18}$ ethoxylated alkyl ether sulfate surfactants used in the instant composition have the structure

$$R-(OCHCH_2)_n OSO_3{}^{M-+}$$

wherein n is about 1 to about 22 more preferably 1 to 3 and R is an alkyl group having about 8 to about 18 carbon atoms, more preferably 12 to 15 and natural cuts, for example, $C_{12-14}$; $C_{12-15}$ and M is an ammonium cation or an alkali metal cation, most preferably sodium or ammonium. The ethoxylated alkyl ether sulfate is present in the composition at a concentration of about 4 wt. % to about 18 wt. %, more preferably about 5 wt. % to 16 wt. %.

The ethoxylated alkyl ether sulfate may be made by sulfating the condensation product of ethylene oxide and $C_{8-10}$ alkanol, and neutralizing the resultant product. The ethoxylated alkyl ether sulfates differ from one another in the number of carbon atoms in the alcohols and in the number of moles of ethylene oxide reacted with one mole of such alcohol. Preferred ethoxylated alkyl ether polyethenoxy sulfates contain 12 to 15 carbon atoms in the alcohols and in the alkyl groups thereof, e.g., sodium myristyl (3EO) sulfate.

Ethoxylated $C_{8-18}$ alkylphenyl ether sulfates containing from 2 to 6 moles of ethylene oxide in the molecule are also suitable for use in the invention compositions. These detergents can be prepared by reacting an alkyl phenol with 2 to 6 moles of ethylene oxide and sulfating and neutralizing the resultant ethoxylated alkylphenol.

The instant composition can contain a mixture of a first sulfonate surfactant which is a magnesium salt of a linear $C_8$–$C_{16}$ alkyl benzene sulfonate such as a magnesium salt of a linear dodecyl benzene sulfonate and a second sulfonate surfactant which is an alkali metal salt of a linear $C_8$–$C_{16}$ alkyl benzene sulfonate such as the sodium salt of linear dodecyl benzene sulfonate. The concentration of the magnesium salt of the linear $C_8$–$C_{16}$ alkyl benzene sulfonate is about 1 wt. % to about 14 wt. %, more preferably about 2 wt. % to about 12 wt. %. The concentration of the alkali metal salt of the alkali metal salt of the linear $C_8$–$C_{16}$ alkyl benzene sulfonate is 1 to about 6 wt. %, more preferably about 1.5 wt. % to about 4 wt. %.

The linear alkyl benzene sulfonate can contain from 10 to 16 carbon atoms in the alkyl group are used in the instant compositions wherein the alkyl benzene sulfonates has a high content of 3- (or higher) phenyl isomers and a correspondingly low content (well below 50%) of 2- (or lower) phenyl isomers, that is, wherein the benzene ring is preferably attached in large part at the 3 or higher (for example, 4, 5, 6 or 7) position of the alkyl group and the content of the isomers in which the benzene ring is attached in the 2 or 1 position.

The instant compositions contain about 4 wt. % to about 16 wt. %, more preferably 5 wt. % to 18 wt. % of an alkyl polysaccharide surfactant. The alkyl polysaccharides surfactants, which are used in conjunction with the aforementioned surfactant have a hydrophobic group containing from about 8 to about 20 carbon atoms, preferably from about 10 to about 16 carbon atoms, most preferably from about 12 to about 14 carbon atoms, and polysaccharide hydrophilic group containing from about 1.5 to about 10, preferably from about 1.5 to about 4, most preferably from about 1.6 to about 2.7 saccharide units (e.g., galactoside, glucoside, fructoside, glucosyl, fructosyl; and/or galactosyl units). Mixtures of saccharide moieties may be used in the alkyl polysaccharide surfactants. The number x indicates the number of saccharide units in a particular alkyl polysaccharide surfactant. For a particular alkyl polysaccharide molecule x can only assume integral values. In any physical sample of alkyl polysaccharide surfactants there will be in general molecules having different x values. The physical sample can be characterized by the average value of x and this average value can assume non-integral values. In this specification the values of x are to be understood to be average values. The hydrophobic group (R) can be attached at the 2-, 3-, or 4- positions rather than at the 1-position, (thus giving e.g. a glucosyl or galactosyl as opposed to a glucoside or galactoside). However, attachment through the 1-position, i.e., glucosides, galactoside, fructosides, etc., is preferred. In the preferred product the additional saccharide units are predominately attached to the previous saccharide unit's 2-position. Attachment through the 3-, 4-, and 6- positions can also occur. Optionally and less desirably there can be a polyalkoxide chain joining the hydrophobic moiety (R) and the polysaccharide chain. The preferred alkoxide moiety is ethoxide.

Typical hydrophobic groups include alkyl groups, either saturated or unsaturated, branched or unbranched containing from about 8 to about 20, preferably from about 10 to about 18 carbon atoms. Preferably, the alkyl group is a straight chain saturated alkyl group. The alkyl group can contain up to 3 hydroxy groups and/or the polyalkoxide chain can contain up to about 30, preferably less than about 10, alkoxide moieties.

Suitable alkyl polysaccharides are decyl, dodecyl, tetradecyl, pentadecyl, hexadecyl, and octadecyl, di-, tri-, tetra-, penta-, and hexaglucosides, galactosides, lactosides, fructosides, fructosyls, lactosyls, glucosyls and/or galactosyls and mixtures thereof.

The alkyl monosaccharides are relatively less soluble in water than the higher alkyl polysaccharides. When used in admixture with alkyl polysaccharides, the alkyl monosaccharides are solubilized to some extent. The use of alkyl monosaccharides in admixture with alkyl polysaccharides is a preferred mode of carrying out the invention. Suitable mixtures include coconut alkyl, di-, tri-, tetra-, and pentaglucosides and tallow alkyl tetra-, penta-, and hexaglucosides.

The preferred alkyl polysaccharides are alkyl polyglucosides having the formula $$RO(C_nH_{2n}O)_r(Z)_x$$

wherein Z is derived from glucose, R is a hydrophobic group selected from the group consisting of alkyl, alkylphenyl, hydroxyalkylphenyl, and mixtures thereof in which said alkyl groups contain from about 10 to about 18, preferably from about 12 to about 14 carbon atoms; n is 2 or 3 preferably 2, r is from 0 to 10, preferably 0; and x is from 1.5 to 8, preferably from 1.5 to 4, most preferably from 1.6 to 2.7. To prepare these compounds a long chain alcohol ($R_2OH$) can be reacted with glucose, in the presence of an acid catalyst to form the desired glucoside. Alternatively the alkyl polyglucosides can be prepared by a two step procedure in which a short chain alcohol ($R_1OH$) can be reacted with glucose, in the presence of an acid catalyst to form the desired glucoside. Alternatively the alkyl polyglucosides can be prepared by a two step procedure in which a short chain alcohol ($C_{1-6}$) is reacted with glucose or a polyglucoside (x=2 to 4) to yield a short chain alkyl glucoside (x=1 to 4) which can in turn be reacted with a longer chain alcohol ($R_2OH$) to displace the short chain alcohol and obtain the desired alkyl polyglucoside. If this two step procedure is used, the short chain alkylglucoside content of the final alkyl polyglucoside material should be less than 50%, preferably less than 10%, more preferably less than about 5%, most preferably 0% of the alkyl polyglucoside.

The amount of unreacted alcohol (the free fatty alcohol content) in the desired alkyl polysaccharide surfactant is preferably less than about 2%, more preferably less than about 0.5% by weight of the total of the alkyl polysaccharide. For some uses it is desirable to have the alkyl monosaccharide content less than about 10%.

The used herein, "alkyl polysaccharide surfactant" is intended to represent both the preferred glucose and galactose derived surfactants and the less preferred alkyl polysaccharide surfactants. Throughout this specification, "alkyl polyglucoside" is used to include alkyl polyglycosides because the stereochemistry of the saccharide moiety is changed during the preparation reaction.

An especially preferred APG glycoside surfactant is Glucopon 625 glycoside manufactured by the Henkel Corporation of Ambler, Pa. Glucopon 625 is a nonionic alkyl polyglycoside characterized by the formula:

$$C_nH_{2n+1}O(C_6H_{10}O_5)_xH$$

wherein n=10 (2%); n=12 (65%); n=14 (21–28%); n=16 (4–8%) and n=18 (0.5%) and x (degree of polymerization) =1.6. Glucopon 625 has: a pH of 6 to 10 (10% of Glucopon 625 in distilled water); a specific gravity at 25° C. of 1.1 g/ml; a density at 25° C. of 9.1 lbs/gallon; a calculated HLB of 12.1 and a Brookfield viscosity at 35° C., 21 spindle, 5–10 RPM of 3,000 to 7,000 cps.

The instant compositions contain about 0.5 to about 4 wt. %, more preferably about 0.75 to about 3.0 wt. % of an ethoxylated $C_{12}$–$C_{14}$ alkyl monoalkanol amide containing 1 to 6 ethoxylated groups such as PEG6 lauramide.

The instant compositions contain about 0.5 wt. % to 5.0% of ethanol and/or isopropanol and about 0 wt. % to about 12 wt. %, more preferably about 1 wt. % to about 10 wt. %, of at least one solubilizing agent which can be sodium xylene sulfonate, sodium cumene sulfonate, a $C_{2-3}$ mono or dihydroxy alkanols such as ethanol, isopropanol and propylene glycol and mixtures thereof. The solubilizing agents are included in order to control low temperature cloud clear properties. Urea can be optionally employed in the instant composition as a supplemental solubilizing agent at a concentration of 0 to about 10 wt. %, more preferably about 0.5 wt. % to about 8 wt. %.

Other solubilizing agents are glycerol, water-soluble polyethylene glycols having a molecular weight of 300 to 600, polypropylene glycol of the formula $HO(CH_3CH_2O)_nH$ wherein n is a number from 2 to 18, mixtures of polyethylene glycol and polypropylene glycol (Synalox).

The instant composition can also contain 0 to about 6 wt. %, more preferably about 0.5 wt. % to about 5 wt. % of an inorganic magnesium containing compound such as magnesium sulfate heptahydrate.

The instant compositions contain a water-soluble zwitterionic surfactant at a concentration of 4 to about 10 wt. %, more preferably about 1.5 wt. % to about 8 wt. %. The zwitterionic surfactant is a water soluble betaine having the general formula:

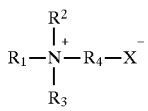

wherein $X^-$ is selected from the group consisting of $CO_2-$ and $SO_3-$ and $R_1$ is an alkyl group having 10 to about 20 carbon atoms, preferably 12 to 16 carbon atoms, or the amido radical:

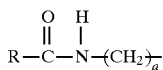

wherein R is an alkyl group having about 9 to 19 carbon atoms and a is the integer 1 to 4; $R_2$ and $R_3$ are each alkyl groups having 1 to 3 carbons and preferably 1 carbon; $R_4$ is an alkylene or hydroxyalkylene group having from 1 to 4 carbon atoms and, optionally, one hydroxyl group. Typical alkyldimethyl betaines include decyl dimethyl betaine or 2-(N-decyl-N,N-dimethyl-ammonia) acetate, coco dimethyl betaine or 2-(N-coco N, N-dimethylammonia) acetate, myristyl dimethyl betaine, palmityl dimethyl betaine, lauryl dimethyl betaine, cetyl dimethyl betaine, stearyl dimethyl betaine, etc. The amidobetaines similarly include cocoamidoethylbetaine, cocoamidopropyl betaine and the like. A preferred betaine is coco ($C_8$–$C_{18}$) amidopropyl dimethyl betaine. Two preferred betaine surfactants are Rewoteric AMB 14U and Goldschmidt Betaine L7.

The composition can also contain 0 to 6 wt. %, more preferably 1 wt. % to 5 wt. % of a sultaine which is preferably a cocoamido-propylhydroxy sultaine. The sultaine can be depicted by the formula:

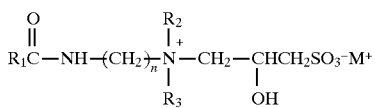

wherein $R_1$ is a saturated or unsaturated alkyl group having about 6 to about 24 carbon atoms, $R_2$ is a methyl or ethyl group, $R_3$ is a methyl or ethyl group, n is about 1 to about 6, and $M^+$ is an alkali metal cation. The most preferred hydroxysultaine is a potassium salt of cocoamidopropyl hydroxysultaine.

An especially preferred APG glycoside surfactant is Glucopon 625 glycoside manufactured by the Henkel Corporation of Ambler, Pa. Glucopon 625 is a nonionic alkyl polyglycoside characterized by the formula:

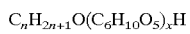

$$C_nH_{2n+1}O(C_6H_{10}O_5)_xH$$

wherein n=10 (2%); n=12 (65%); n=14 (21–28%); n=16 (4–8%) and n=18 (0.5%) and x (degree of polymerization) =1.6. Glucopon 625 has: a pH of 6 to 10 (10% Glucopon 625 in distilled water); a specific gravity at 25° C. of 1.1 g/ml; a density at 25° C. of 9.1 lbs/gallon; a calculated HLB of 12.1 and a Brookfield viscosity at 35° C., 21 spindle, 5–10 RPM of 3,000 to 7,000 cps.

Amine oxide semi-polar nonionic surfactants used in the instant compositions comprise compounds and mixtures of compounds having the formula

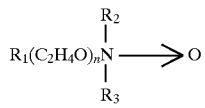

wherein $R_1$ is an alkyl, 2-hydroxyalkyl, 3-hydroxyalkyl, or 3-alkoxy-2-hydroxypropyl radical in which the alkyl and alkoxy, respectively, contain from 8 to 18 carbon atoms, $R_2$ and $R_3$ are each methyl, ethyl, propyl, isopropyl, 2-hydroxyethyl, 2-hydroxypropyl, or 3-hydroxypropyl, and n is from 0 to 10. Particularly preferred are amine oxides of the formula:

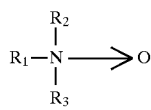

wherein $R_1$ is a $C_{12-16}$ alkyl, or cocoamidopropyl group and $R_2$ and $R_3$ are methyl or ethyl. The above ethylene oxide condensates, amides, and amine oxides are more fully described in U.S. Pat. No. 4,316,824 which is hereby incorporated herein by reference. Preferred amine oxides are lauryl amine oxide and cocoamido propyl amine oxide. The concentration of the amine oxide in the instant compositions is 0 to 8 wt. %, more preferably 1 to 7 wt. %.

The instant formulas explicitly exclude alkali metal silicates and alkali metal builders such as alkali metal polyphosphates, alkali metal carbonates, alkali metal phosphonates and alkali metal citrates because these materials, if used in the instant composition, would cause the composition to have a high pH as well as leaving residue on the surface being cleaned. The final essential ingredient in the inventive compositions having improved interfacial tension properties is water.

In final form, the instant compositions exhibit stability at reduced and increased temperatures. More specifically, such compositions remain clear and stable in the range of 5° C. to 50° C., especially 10° C., to 43° C. The instant compositions have a light transmission of at least 95%. Such compositions exhibit a pH of 5 to 8. The liquid compositions are readily pourable and exhibit a viscosity in the range of 100 to 600 cps as measured at 25° C. with a Brookfield RVT Viscometer using a #2 spindle rotating at 30 RPM. Preferably, the viscosity is maintained in the range of 300 to 500 cps. The instant compositions have a minimum foam height of 320 mls after 40 rotation at 25° C. as measured by the foam volume test. The foam test is an inverted cylinder test. 100 mls of 0.033 wt. % LDL formula in 150 ppm of $H_2O$ is placed in a stoppered graduate cylinder (500 mls) and inverted 40 cycles at a rate of 30 cycles/minute. After 40 inversions, the foam volume which has been generated is measured in mls inside the graduated cylinder.

The following examples illustrate liquid cleaning compositions of the described invention. Unless otherwise specified, all percentages are by weight. The exemplified compositions are illustrative only and do not limit the scope of the invention. Unless otherwise specified, the proportions in the examples and elsewhere in the specification are by weight.

EXAMPLE 1

The following composition in wt. % was prepared by simple mixing procedure at 25° C.:

|  | A | B | C | D |
|---|---|---|---|---|
| AEOS 1.3 EO | 8.4 | 8.4 | 8.4 | 8.4 |
| APG625 | 9.7 | 9.7 | 9.7 | 9.7 |
| Magnesium linear dodecyl benzene sulfonate | 7.4 | 7.4 | 7.4 | 7.4 |
| Sodium linear dodecyl benzene sulfonate | 2.9 | 2.9 | 2.9 | 2.9 |
| CAP amine oxide | 3.7 | — | — | — |
| Alkyl amine oxide | — | 3.7 | — | — |
| CAP hydroxysultaine | — | — | 3.7 | — |
| Cocoamidopropyl betaine | 5.8 | 5.8 | 5.8 | 9.5 |
| PEG-6 lauramide | 0.9 | 0.9 | 0.9 | 0.9 |
| Ethanol | 3.4 | 3.4 | 3.4 | 3.4 |
| Hydrotrope | 0.2 | 0.45 | 0.2 | 0.2 |
| Water & Minors | Bal. | Bal. | Bal. | Bal. |
| Shake foam volume after 40 rotations (ml) | 248 | 202 | 265 | 250 |
| Shake foam volume with soil after 40 rotations (ml) | 22 | 15 | 23 | 23 |
| Baumgartner lard removal (mg) | 31 | 30 | 34 | 28 |

What is claimed:

1. A clear light duty liquid cleaning composition which comprises approximately by weight:
   (a) 4% to 18% of an alkali metal or ammonium salt of a $C_{8-18}$ ethoxylated alkyl ether sulfate;
   (b) 4% to 12% of a betaine surfactant;
   (c) 1% to 6% of a sodium salt of a linear $C_8$–$C_{16}$ alkyl benzene sulfonate surfactant;
   (d) 0% to 12% of at least one solubilizing agent;
   (e) 4% to 16 % of an alkyl polyglucoside surfactant;
   (f) 0 to 8% of an amine oxide;
   (g) 0.2 to 4% of an ethoxylated $C_{12}$–$C_{14}$ alkyl monoalkanol amide;
   (h) 1% to 14 % of a magnesium salt of a linear $C_8$–$C_{16}$ alkyl benzene sulfonate surfactant; and
   (i) the balance being water.

2. The composition of claim 1, wherein said solubilizing agent is a $C_{2-4}$ mono or dihydroxy alkanol.

3. The composition of claim 1, wherein said solubilizing agent is selected from the group consisting of isopropanol, ethanol and propylene glycol and mixtures thereof.

4. The composition of claim 1, wherein said solubilizing agent is selected from the group consisting of glycerol, polyethylene glycols, polypropylene glycol of the formula $HO(CH_3)CHCH_2O)_nH$, wherein n is 2 to 18.

5. The composition of claim 1, further including a magnesium inorganic containing compound.

6. The composition of claim 1, further including a cocoamido propyl hydroxy sultaine.

* * * * *